United States Patent
Chavan et al.

(10) Patent No.: US 9,295,625 B2
(45) Date of Patent: Mar. 29, 2016

(54) PHOTOSTABLE SUNSCREEN COMPOSITION

(71) Applicant: Conopco, Inc., Englewood Cliffs, NJ (US)

(72) Inventors: Mohan Vijaykumar Chavan, Mumbai (IN); Charu Duggal, Kanpur (IN); Kumar Gaurav, Hazaribag (IN); Janhavi Sanjay Raut, Bangalore (IN); Ashish Anant Vaidya, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/419,284

(22) PCT Filed: Jul. 2, 2013

(86) PCT No.: PCT/EP2013/063888
§ 371 (c)(1),
(2) Date: Feb. 3, 2015

(87) PCT Pub. No.: WO2014/023481
PCT Pub. Date: Feb. 13, 2014

(65) Prior Publication Data
US 2015/0224042 A1  Aug. 13, 2015

(30) Foreign Application Priority Data
Aug. 6, 2012  (EP) .................................... 12179361

(51) Int. Cl.
| A61K 8/49 | (2006.01) |
| A61Q 17/04 | (2006.01) |
| A61K 8/86 | (2006.01) |
| A61K 8/35 | (2006.01) |
| A61K 8/37 | (2006.01) |
| A61Q 15/00 | (2006.01) |

(52) U.S. Cl.
CPC .................. *A61K 8/4966* (2013.01); *A61K 8/35* (2013.01); *A61K 8/37* (2013.01); *A61K 8/86* (2013.01); *A61Q 17/04* (2013.01); *A61K 2800/49* (2013.01); *A61K 2800/52* (2013.01); *A61Q 15/00* (2013.01)

(58) Field of Classification Search
None
See application file for complete search history.

(56) References Cited

U.S. PATENT DOCUMENTS

| 6,248,311 | B1 | 6/2001 | Candau |
| 2004/0062729 | A1 | 4/2004 | Candau |
| 2006/0002872 | A1 | 1/2006 | Candau |
| 2007/0140997 | A1 | 6/2007 | Candau |

FOREIGN PATENT DOCUMENTS

| DE | 19841797 | 3/2000 |
| DE | 19841798 | 3/2000 |
| DE | 102007024342 | 11/2008 |
| EP | 1634624 | 3/2006 |
| FR | 2872417 | 1/2006 |
| FR | 2872417 A1 * | 1/2006 |
| FR | 2924020 | 5/2009 |
| GB | 2412866 | 10/2005 |
| GB | 2412866 A * | 10/2005 |
| GB | 2439618 | 1/2008 |
| WO | WO9703642 | 2/1997 |
| WO | WO0185123 | 11/2001 |
| WO | WO2005117824 | 12/2005 |
| WO | WO2006003020 | 1/2006 |
| WO | WO2007144670 | 12/2007 |
| WO | WO2008022946 | 2/2008 |
| WO | WO2010129318 | 11/2010 |

OTHER PUBLICATIONS

IPRP2 in PCTEP2013063888 dated Nov. 21, 2014, pp. 1-13.
Search Report in PCTEP2013063888 dated Feb 6, 2014, pp. 14-17.
Search Report in EP12179361 dated Feb. 21, 2013, pp. 18-21.
Written Opinion 1 in PCTEP2013063888 dated Feb. 6, 2013, pp. 22-28.
Written Opinion 2 in PCTEP2013063888 dated Aug. 6, 2014, pp. 29-34.
Written Opinion in EP12179361 dated Feb. 21, 2013, pp. 35-38.

* cited by examiner

*Primary Examiner* — Robert A Wax
*Assistant Examiner* — Melissa Mercier
(74) *Attorney, Agent, or Firm* — Greenberg Traurig, LLP

(57) ABSTRACT

The invention relates to a photostable sunscreen composition that not only provides enhanced sun protection by way of high SPF, but does that over sustained period of time after applying the composition on the skin. The present inventors have found that when a compound of the triazine group is used without additional UVA or UVB sunscreen, and a non-ionic surfactant is included in a cosmetic base comprising fatty acids, it is possible to achieve high SPF.

10 Claims, No Drawings

PHOTOSTABLE SUNSCREEN COMPOSITION

FIELD OF THE INVENTION

The invention relates to a photostable sunscreen composition. The invention more particularly relates to a sunscreen composition that not only provides enhanced sun protection by way of high SPF, but does that over sustained period of time after applying the composition on the skin.

BACKGROUND OF THE INVENTION

Solar radiation includes ultraviolet (UV) radiation, wavelength of which is between 200 nm and 400 nm. Exposure of skin to UV-A (320 to 400 nm) and UV-B (290 to 320 nm) causes various problems like reddening of the skin, localized irritation, sunburn, melanoma and formation of wrinkles. UV radiation is also known to cause damage to hair. Therefore, it is desirable to protect the skin and other keratinous substrates of the human body from the harmful effects of both UV-A and UV-B radiation.

SPF (Sun Protection Factor) is a measure of the protection from solar radiation. In order to achieve this, formulators generally include high amounts of UV-A and UV-B. The present inventors have found when compound of the triazine group is used without additional UVA or UVB sunscreen, when non-ionic surfactant is included in a cosmetic base comprising fatty acids, it is possible to provide high SPF.

Compounds of triazine group have been included in sunscreen compositions. WO07/144670 (Reckitt & Colman) discloses a skincare composition in the form of an emulsion comprising: a) an organic sunscreen component comprising at least one sunscreen selected from the group consisting of bis-ethylhexyloxyphenol methoxyphenyl triazine and methylene bis-benzotriazolyl tetramethylbutylphenol; b) a moisturising system comprising starch or a derivative thereof and a polymeric quaternary compound salt having humectant properties; and c) a carrier comprising an oil phase, an aqueous phase and an emulsifying system, said emulsifying system comprising at least one emulsifier selected from an anionic or non-ionic emulsifier. The composition is claimed to not only reduce the effect of UV radiation on the skin from UV damage, it also improves the moisturisation levels to help protect the skin from the effects of UV radiation.

EP1634624 (L'Oreal, 2006) discloses a cosmetic or dermatological photoprotective composition which comprises at least 1,3,5-triazine derivative (I) and arylalkyl benzoate derivative (II) to improve the factor of solar protection, cosmetic properties and/or stability of (A).

Non-ionic surfactants have been disclosed in the past for use in skin compositions. WO2008/022946 (Unilever) discloses a photostable cosmetic composition comprising 0.1 to 10% dibenzoylmethane or its derivative, 0.1 to 10% by weight p-methoxycinnamic acid or its derivative, 0.5 to 8% by weight C8 to C18 fatty alcohol ethoxylate and 0.5 to 8% polyalkyleneglycol.

The prior art does not disclose stable sunscreen compositions which comprise triazine compounds and whose sunprotection is enhanced specifically through use of non-ionic surfactants in a fatty acid containing oil-in-water emulsion.

It is thus an object of the present invention to obviate the drawbacks of the prior art and provide high SPF photo-protective sunscreen compositions.

Another object of the present invention is to achieve the above object using relatively low amounts of sunscreen agents thereby keeping costs low.

SUMMARY OF THE INVENTION

The present invention provides for a sunscreen composition comprising,
(a) 0.05 to 15% by weight compound of formula A;

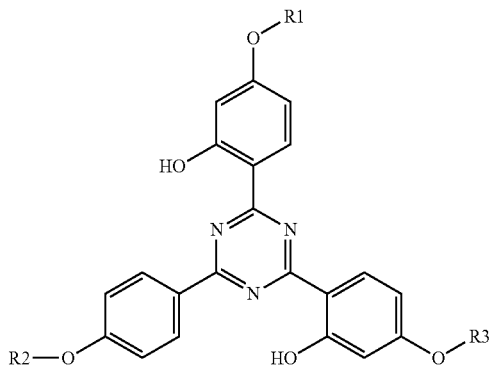

where R1, R2 and R3 are each selected from any one of alkyl, branched alkyl, cycloalkyl, polycycloalkyl, heterocycloalkyl, alkaryl, alkoxy, aryl, aralkyl, alkenyl, alkynyl or fluorocarbon groups containing 1 to 50 carbon atom(s)
(b) 0.01% to 10% by weight a non-ionic surfactant;
(c) a cosmetically acceptable base comprising 3 to 25% fatty acid by weight of the composition.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive.

It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "A Sunscreen Composition" as used herein, is meant to include a composition for topical application to sun-exposed areas of the skin and/or hair of mammals, especially humans. Such a composition may be generally classified as leave-on or rinse off, and includes any product applied to a human body for also improving appearance, cleansing, odor control or general aesthetics. It is more preferably a leave-on product. The composition of the present invention can be in the form of a liquid, lotion, cream, foam, scrub, gel, or toner, or applied with an implement or via a face mask, pad or patch. Non-limiting examples of such sunscreen compositions include leave-on skin lotions, creams, antiperspirants, deodorants, lipsticks, foundations, mascara, sunless tanners and sunscreen lotions. "Skin" as used herein is meant to include skin on the face and body (e.g., neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

An advantage of the present invention is that the sunscreen composition is capable of providing an SPF of higher than 20, more preferably at least 30, further more preferably higher than 40. It is preferred that the composition comprises at the most 10% total organic sunscreens by weight of the composition.

The composition of the invention comprises 0.05 to 15% by weight compound of the formula A:

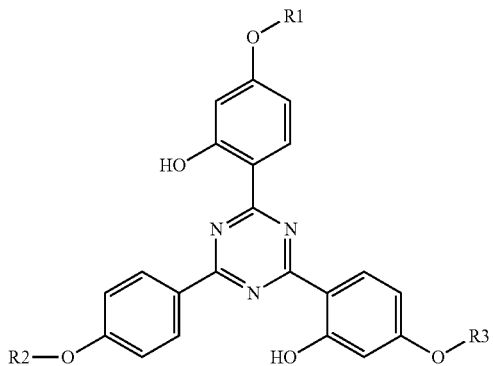

where R1=C1-C30 alkyl group (linear and branched);

Compound of formula A is preferably present in 0.1 to 10%, more preferably 0.1 to 7% by weight of the composition. In the compound of formula A, R1, R2 and R3 are each selected from any one of alkyl, branched alkyl, cycloalkyl, polycycloalkyl, heterocycloalkyl, alkaryl, alkoxy, aryl, aralkyl, alkenyl, alkynyl or fluorocarbon groups containing 1 to 50 carbon atom(s).

Preferred compound of formula A is 2,4-Bis-{[4-(2-ethylhexyl-oxy)-2-hydroxy]-phenyl}-6-(4-methoxy-phenyl)-(1,3,5)-triazine commercially sold under the brand names Tinosorb S (available from BASF) or Escalol S (available from Ashland Inc).

An important ingredient that contributes to the benefits of the present invention is a non-ionic surfactant. The non-ionic surfactant for use in the composition of the present invention has an HLB value of at least 9.

HLB is calculated using the Griffin method wherein HLB=20×Mh/M wherein Mh is the molecular mass of the hydrophilic portion of the molecule and M is the molecular mass of the whole molecule, giving a result on an arbitrary scale of 0 to 20. Typical values for various surfactants are given below:

A value<10: Lipid soluble (water insoluble)
A value>10: Water soluble
A value from 4 to 8 indicates an anti-foaming agent
A value from 7 to 11 indicates a W/O (water in oil) emulsifier
A value from 12 to 16 indicates oil in water emulsifier
A value from 11 to 14 indicates a wetting agent
A value from 12 to 15 is typical of detergents
A value of 16 to 20 indicates a solubiliser or hydrotrope The non-ionic surfactant is preferably selected from any one of the following groups:
(a) fatty alcohol ethoxylates with saturated carbon chain and having HLB higher than 15.5; or
(b) fatty alcohol ethoxylates with unsaturated carbon chain with HLB higher than 12.
(c) alkyl phenol ethoxylates having HLB higher than 15;
(d) polyoxyethylene sorbitan alkyl esters with saturated C12 to C16 carbon chain and having HLB higher than 12;
(e) polyoxyethylene sorbitan alkyl esters with unsaturated C18 carbon chain and having HLB higher than 9;

Suitable commercially available examples of (a) fatty alcohol ethoxylates with saturated carbon chain and having HLB higher than 15.5 or from (b) the class of fatty alcohol ethoxylates with unsaturated carbon chain with HLB higher than 12 are sold under the brand names Brij 35 (a C12EO23 compound), Brij 97 (unsaturated C18EO12), Brij 700 (C18EO100) or Brij 99 (unsaturated C18EO20). Suitable examples of (c) alkyl phenol ethoxylates with HLB higher than 15 for use in the composition of the invention are sold under the brand names Triton X 165, Triton X 305, Triton 405, or Triton X 705. Suitable examples of (d) polyoxyethylene sorbitan alkyl esters with saturated C12 to C16 carbon chain and having HLB higher than 12 and (e) polyoxyethylene sorbitan alkyl esters with unsaturated C18 carbon chain and having HLB higher than 9 are sold under the brand names Tween20, Tween21, Tween40, Tween80, Tween 81 or Tween85 trioleate. The non-ionic surfactant is included in 0.1 to 5%, preferably 0.2 to 4%, more preferably 0.2 to 3% by weight of the composition.

The composition of the invention comprises a cosmetically acceptable base comprising 3 to 25% fatty acid by weight of the composition. Cosmetically acceptable bases are preferably in a cream, lotion, gel or emulsion format. A more preferred format is a cream, further more preferred a vanishing cream. Preferred compositions of the invention comprise 3 to 20% and more preferably 6 to 20% fatty acid (saturated or unsaturated fatty acids or their mixtures) by weight of the composition. The composition preferably also comprises 0.1 to 10%, more preferably 0.1 to 3% soap. $C_{12}$ to $C_{20}$ fatty acids are especially preferred in vanishing cream bases, further more preferred being $C_{14}$ to $C_{18}$ fatty acids. In creams, the fatty acid is preferably substantially a mixture of stearic acid and palmitic acid. Soaps in the vanishing cream base include alkali metal salt of fatty acids, like sodium or potassium salts. The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the vanishing cream base is within the scope of the present invention. The cosmetically acceptable base is usually from 10 to 99.9%, preferably from 50 to 99% by weight of the composition. The composition of the invention is preferably an oil-in-water emulsion composition. The cosmetically acceptable base preferably includes water. Water is preferably included in 35 to 90%, more preferably 50 to 85%, further more preferably 50 to 80% by weight of the composition.

The composition of the invention preferably comprises an additional UV-A or UV-B sunscreen, other than the compound of formula A. These sunscreens are preferably chosen from compounds of the following seven major groups: (1) benzophenones, (2) anthranilates, (3) dibenzoylmethanes (4) salicylates, (5) cinnamates, (6) camphores and (7) p-amino benzoic acids (PABA) or mixtures.

The preferred UVA sunscreen for use in the composition of the invention is a compound of the dibenzoylmethane class.

Preferred dibenzoylmethane derivative are selected from 4-tert-butyl-4'-methoxydibenzoylmethane, 2-methyldibenzoylmethane, 4-methyl-dibenzoyl-methane, 4-isopropyldibenzoyl-methane, 4-tert-butyldibenzoyl-methane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane. The composition of the invention preferably comprises 0.1 to 5%, more preferably 0.2 to 5%, further more preferably 0.4 to 3%, compound of the dibenzoylmethane class by weight of the composition.

The additional UV-B organic sunscreen which may be included in the composition of the invention is preferably oil soluble. It is preferably selected from the class of cinnamic acid, salicylic acid, diphenyl acrylic acid compounds. A few of the preferred oil soluble UV-B sunscreens which are commercially available and useful for inclusion in the composition of the invention are Octisalate™, Homosalate™, Neo-Helipan™, Octocrylene™, Oxybenzone™ or Parsol MCX™. The composition of the invention preferably comprises 0.1 to 7%, more preferably 0.2 to 5%, further more preferably 0.4 to 3% UV B sunscreen, by weight of the composition. A useful aspect of the present invention is that high SPF values can be obtained even when the total amount of organic sunscreens (excluding the compound of formula A) are present in small amounts which may be in the range of 0.1 to 7%, preferably from 0.5 to 6%, more preferably 1 to 5%, by weight of the composition.

Other useful photostabilizers may be preferably used in the present invention. This include derivatives of diphenylacrylate, benzylidene camphor, napthalate, fluorene and diarylbutadiene etc.

The composition of the invention preferably includes solubilisers to enhance the solubility of compound of formula A, thereby increasing its sun-protection efficacy. Solubilisers are preferably of the class of esters of aryl alcohol, akyl or cycloalkyl carboxylic acid or carbonic acid. Of these, the class of esters of aryl alcohol is preferred for use as a solubliser. Preferred solubilisers are phenethyl, benzyl or substitued benzyl alcohols. Most preferred solubilisers may be selected from the compounds given below:

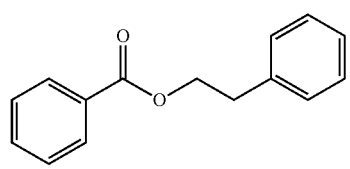

X-Tend™ 226 (phenethyl benzoate)

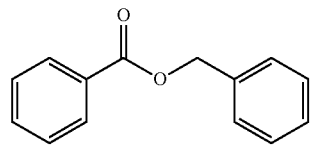

benzyl benzoate

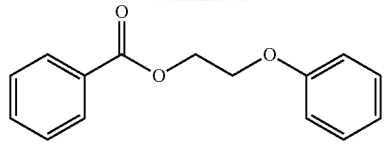

2-phenoxyethyl benzoate

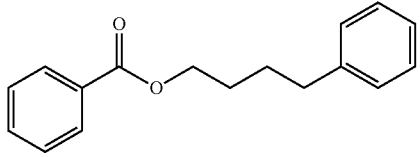

2-phenylbutyl benzoate

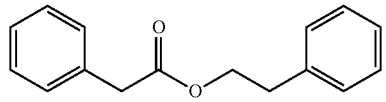

2-phenylethyl phenylacetate

Solublisers are preferably included in 0.1 to 15%, more preferably in 0.5 to 10%, further more preferably 0.5 to 5% by weight of the composition.

Other useful sun-protective agents e.g. inorganic sunblocks may be preferably used in the present invention. These include, for example, zinc oxide, iron oxide, silica, such as fumed silica, or titanium dioxide. The total amount of sun block that is preferably incorporated in the composition according to the invention is from 0.1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The composition of the invention may comprise a conventional deodourant base as the cosmetically acceptable carrier. By a deodorant is meant a product in the stick, roll-on, or propellant medium which is used for personal deodorant benefit e.g. application in the under-arm or any other area which may or may not contain anti-perspirant actives.

Deodorant compositions can generally be in the form of firm solids, soft solids, gels, creams, and liquids and are dispensed using applicators appropriate to the physical characteristics of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The invention is now further described by way of the following non-limiting examples.

EXAMPLES

Examples A to C and 1 to 4

SPF Obtained with Compositions Outside the Invention (a to C) and Those within the Invention (1 to 4)

Photoprotective personal care vanishing cream compositions as shown in Table 1 were prepared. In vitro-SPF was measured for all the samples using a Optometrics 290S instrument model. The substrate used was a 8 cm Transpore tape procured from 3M Company. The sample was applied at 2 mg/cm². The SPF as measured is shown in Table 1.

TABLE 1

|  | Examples | | | | | | |
| --- | --- | --- | --- | --- | --- | --- | --- |
|  | A | B | C | 1 | 2 | 3 | 4 |
| Hystric acid, wt % | 17.0 | 17.0 | 17.0 | 17.0 | 17.0 | 17.0 | 17.0 |
| Potassium hydroxide, wt % | 0.6 | 0.6 | 0.6 | 0.6 | 0.6 | 0.6 | 0.6 |
| Surfactant | — | Potassium Cetyl phosphate | Potassium Stearate | Brij L 23 | Brij L 23 | Brij L 23 | Brij L 23 |
| Surfactant, wt % | — | 5.0 | 3.0 | 2.0 | 5.0 | 2.0 | 2.0 |
| Tinosorb S wt % | 5.0 | 5.0 | 5.0 | 5.0 | 5.0 | 7.0 | 5.0 |
| Parsol MCX | — | — | — | — | — | — | 2.25 |
| Water | To 100 | To 100 | To 100 | To 100 | To 100 | To 100 | To 100 |
| SPF | 18 | 15 | 18 | 38 | 60 | 78 | 100 |

In the Table 1 above the following compounds are referred to Brij L23: with n=12 and m=23 has the following general structure and was sourced from Croda. It is also sold under the brand name of Brij-35. It has HLB value of 16.9.

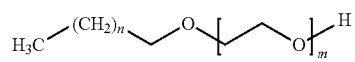

Tinosorb S: has the following structure and was sourced from BASF

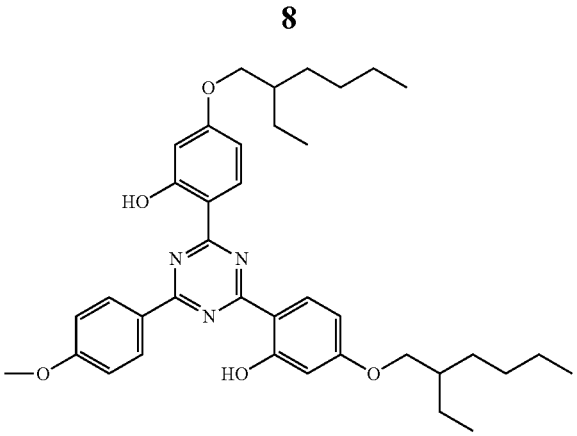

Parsol MCX: has the following structure and was sourced from Chem Spec.

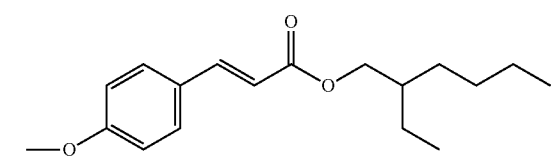 [SMILES: CCCCC(CC)COC(=O)/C=C/c1ccc(OC)cc1]

The data in Table-1 indicates that compositions as per the invention (Examples 1 to 4) provide for vastly superior SPF values as compared to compositions outside the invention (Examples A to C).

Examples D and 5, 6

Photostability of Compositions of the Invention (5 & 6) as Compared to Control (Example D)

Photoprotective personal care vanishing cream compositions as shown in Table-2 were prepared. The compositions were measured for photostability using the following procedure:

The compositions were applied (~2 mg/cm2) on two clean glass plates to generate thin films of uniform thickness. Out of these, one plate was exposed to Atlas solar simulated radiations (UVA flux, 5.5 mW/cm² for 60 minutes of UV exposure. The other plate was kept un-exposed which served as control. Subsequent to completion of the above protocol, all the films of the cream were separately extracted in HPLC grade methanol. The quantification of the active was done using Perkin Elmer UV/Visible Spectrometer or High Performance Liquid chromatography (HPLC). The absorbance at a scanning range of 200-800 nm was measured for each solution, using quartz cuvette and respective blank solutions on a spectrometer. Relative absorbance values were recorded at a wavelength of 355 nm (for UVA). % photostability of the UV-A sunscreen was determined and plotted against time of exposure. UVR for exposure was generated using a solar simulator (Atlas kW system) with a irradiance of 5.5 mJ cm⁻², at a distance of ~20 cm. The irradiance was measured using a radiometer (Solar Light Co. PMA2200UV). Relative absorbance values were recorded at a wavelength of 310 nm (for UVB). % photostability of the UV-B sunscreen was determined and plotted against time of exposure.

The photostability of the UVA and UVB sunscreen is shown in Table 2.

TABLE 2

| | Examples | | |
|---|---|---|---|
| | D | 5 | 6 |
| Hystric acid, wt % | 17.0 | 17.0 | 17.0 |
| Potassium hydroxide, wt % | 0.6 | 0.6 | 0.6 |
| Brij 35, wt % | 2.0 | 2.0 | 2.0 |
| Tinosorb S wt % | — | 2.5 | 2.5 |
| Parsol 1789 | 2.25 | 2.25 | — |
| Parsol MCX | 1.2 | 1.2 | 1.2 |
| Water | To 100 | To 100 | To 100 |
| SPF | 18 | 15 | 18 |
| % UVA remaining after 60 minutes | 32 | 90 | 95 |
| % UVB remaining after 60 minutes | 15 | 85 | 86 |

Parsol 1789: has the following structure and was sourced from Chem Spec

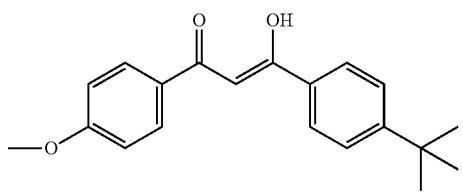 [SMILES: COc1ccc(C(=O)/C=C(\O)c2ccc(C(C)(C)C)cc2)cc1]

The data in Table 2 indicates that compositions as per the invention (Examples 5 and 6) provide for vastly superior UVA and UVB stability as compared to a control sample Example D (outside the invention).

Examples E and 7 to 9

Effect of Fatty Acid Concentration

Photoprotective personal care cream compositions as shown in Table 3 were prepared and the In vitro-SPF was measured similar to the Examples 1 to 4. The SPF values as measured are shown in Table 3.

TABLE 3

| | Examples | | | |
|---|---|---|---|---|
| | E | 7 | 8 | 9 |
| Hystric acid, wt % | — | 5.0 | 10.0 | 17.0 |
| Potassium hydroxide, wt % | 0.6 | 0.6 | 0.6 | 0.6 |
| Brij 35, wt % | 5.0 | 5.0 | 5.0 | 5.0 |
| Tinosorb S wt % | 5.0 | 5.0 | 5.0 | 5.0 |
| Carbopol Ultrez 20 | 0.6 | 0.6 | 0.6 | 0.6 |
| Water | To 100 | To 100 | To 100 | To 100 |
| SPF | 7 | 21 | 42 | 60 |

Carbopol ® Ultrez 20 (INCI: Acrylates/C10-30 Alkyl Acrylate Crosspolymer) was procured from Lubrizol.

The data in Table 3 indicates that inclusion of fatty acid within the claimed concentration range provides for vastly enhanced SPF.

Examples F, 10-11

Effect of Inclusion of Solubilisers

Compositions as shown in Table 4 below were prepared. The in-vitro SPF was measured using the procedure already mentioned earlier. The SPF values of the various compositions are given in Table 4.

TABLE 4

| | Examples | | |
|---|---|---|---|
| | F | 10 | 11 |
| Hystric acid, wt % | 17.0 | 17.0 | 17.0 |
| Potassium hydroxide, wt % | 0.6 | 0.6 | 0.6 |
| Surfactant | Brij -35 | Brij - 35 | Brij - 35 |
| Surfactant, wt % | 2.0 | 2.0 | 2.0 |
| Tinosorb S wt % | 3.75 | 3.75 | 3.75 |
| Solubiliser used | — | IPM | X-TEND 226 |
| Solubiliser, wt % | — | 1.0 | 1.0 |
| Water | To 100 | To 100 | To 100 |
| SPF | 15.7 | 23.3 | 27.5 |

In the above table,
IPM is Iso-propyl myristate
X-TEND 226 is phenethyl benzoate The data in Table 4 indicates that inclusion of a solubiliser (Example 10) provides for enhanced SPF while inclusion of a preferred solubliser as per the invention (Example 11) provides further enhanced SPF.

We claim:
1. A photostable sunscreen composition comprising,
(a) 0.05 to 15% by weight compound of formula A;

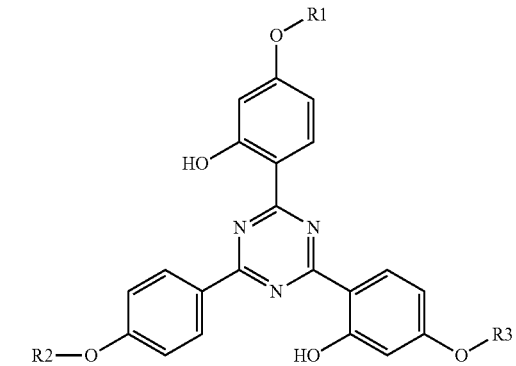

where R1, R2 and R3 are each selected from any one of alkyl, branched alkyl, cycloalkyl, polycycloalkyl, heterocycloalkyl, alkaryl, alkoxy, aryl, aralkyl, alkenyl, alkynyl or fluorocarbon groups containing 1 to 50 carbon atom(s);
(b) 0.01% to 10% by weight a non-ionic surfactant; selected from the group consisting of:
(a) fatty alcohol ethoxylates with saturated carbon chain and having HLB higher than 15.5;
(b) fatty alcohol ethoxylates with unsaturated carbon chain with HLB higher than 12;
(c) alkyl phenol ethoxylates having HLB higher than 15;
(d) polyoxyethylene sorbitan alkyl esters with saturated C12 to C16 carbon chain and having HLB higher than 12; and
(e) polyoxyethylene sorbitan alkyl esters with unsaturated C18 carbon chain and having HLB higher than 9; and
(c) a cosmetically acceptable base comprising 6 to 20% fatty acid by weight of the composition.
2. A composition as claimed in claim 1 wherein R1 is C1-C30 alkyl group.
3. A composition as claimed in claim 1 wherein the cosmetically acceptable base comprises 0.1 to 10% by weight soap.

4. A composition as claimed in claim 1, comprising 0.01 to 10% by weight of UVA or UVB sunscreens selected from the group consisting of (1) benzophenones, (2) anthranilates, (3) dibenzoylmethane (4) salicylates, (5) cinnamates, (6) camphores (7) p-amino benzoic acid (PABA) compounds and their mixtures.

5. A composition as claimed in claim 4, wherein said dibenzoylmethane is present from 0.1% to 5% by weight.

6. A composition as claimed in claim 4 comprising 0.1 to 7% by weight of an oil soluble UV-B organic sunscreen.

7. A composition as claimed in claim 6 wherein said oil soluble UV-B organic sunscreen is selected from the group consisting of cinnamic acid, salicylic acid, and diphenyl acrylic acid compounds.

8. A composition as claimed in claim 6, wherein said oil-soluble UV-B sunscreen is 2-ethyl-hexyl-4-methoxy cinnamate.

9. A composition as claimed in claim 1 comprising at the most 10% total organic sunscreens.

10. A composition as claimed in claim 1 comprising a solubiliser selected from the group consisting of a class of esters of aryl alcohol, alkyl or cycloalkyl carboxylic acid, carbonic acid, and mixtures thereof.

\* \* \* \* \*